United States Patent
Ortega et al.

[11] Patent Number: 6,064,717
[45] Date of Patent: May 16, 2000

[54] UNRESTRICTED MOTION APPARATUS AND METHOD FOR X-RAY DIFFRACTION ANALYSIS

[75] Inventors: Richard Ortega; Delrose Winter, both of Austin, Tex.

[73] Assignee: Rigaku/USA, Inc., Danvers, Mass.

[21] Appl. No.: 08/975,630

[22] Filed: Nov. 21, 1997

[51] Int. Cl.$^7$ .................................................. G01N 23/20
[52] U.S. Cl. .................. 378/71; 378/73; 378/79
[58] Field of Search ........................... 378/71, 73, 79–81

[56] References Cited

U.S. PATENT DOCUMENTS

| | | |
|---|---|---|
| 4,501,011 | 2/1985 | Hauck et al. ............................. 378/196 |
| 4,735,451 | 4/1988 | Wojciechowski et al. .......... 294/103.1 |
| 4,807,273 | 2/1989 | Haendle .................................... 378/116 |
| 4,881,177 | 11/1989 | McClean et al. ........................ 364/513 |
| 5,014,293 | 5/1991 | Boyd et al. ............................... 378/197 |
| 5,318,254 | 6/1994 | Shaw et al. ............................... 244/134 |
| 5,490,646 | 2/1996 | Shaw et al. ............................... 244/134 |
| 5,602,889 | 2/1997 | Oldendorf et al. ........................ 378/29 |
| 5,603,243 | 2/1997 | Finley ..................................... 74/490.07 |

FOREIGN PATENT DOCUMENTS 2645007  of 0000  France .

*Primary Examiner*—Craig E. Church
*Attorney, Agent, or Firm*—J. Nevin Shaffer, Jr.; Shaffer & Culbertson, LLP

[57] ABSTRACT

An unrestricted motion device (10) has a sample holder (12), a detector holder (14) capable of independent multi-dimensional movement, a radiation source (16) and a radiation source holder (42) also capable of independent, multi-dimensional movement. In a preferred embodiment, the radiation source (16) is an x-ray tube. A controller (18) is connected to the sample holder (12) and detector holder (14) as well as to radiation source (16) so as to enable control of the independent movement of the sample holder (12) and detector holder (14), as well as operation of radiation source (16) and independent movement of radiation source (16). So long as any two of the sample holder (12), detector holder (14) or radiation source holder (42) are capable of multi-dimensional, independent movement, the entire diffraction cone (40) can be observed and analyzed. In a preferred embodiment, the holders are robots. Samples 34 of any size, weight or shape are hereby capable of analysis simply and easily and further, by means of controller (18), local amendment, modification, and customizing of the data collection scheme is enabled. By replacing the prior art goniometer (46) with individual independent robots, such that the sample holder (12) is not physically attached or coupled to the robot moving the detector (36) or the robot moving the radiation source (16), the restrictions on sample size, weight and shape are removed. Also, restrictions on coverage of reciprocal space are greatly reduced since the detector (36), radiation source (16) and/or sample holder (12) can be moved out of plane to any location in the robot's accessible envelope of reach. Also, the need for numerous sample holders (12) capable of different axial motions is eliminated and automatic sample changing and tube changing from point to line mode is enabled.

7 Claims, 2 Drawing Sheets

UNRESTRICTED MOTION APPARATUS AND METHOD FOR X-RAY DIFFRACTION ANALYSIS

BACKGROUND OF THE INVENTION

This invention relates to an apparatus and method of performing x-ray diffraction analysis. In particular, this invention relates to performing x-ray diffraction on large (over 12 cm in diameter) parts or in assembly line environments. This is accomplished by decoupling sample movement from the movement of a detector and x-ray source by replacing the goniometer base used in conventional x-ray diffraction instruments. The goniometer base is replaced with holders (robots) which move the x-ray source and/or detector independently such that the x-ray source or detector are not physically attached to the sample.

In addition to eliminating the inherent restrictions placed on the sample size by the prior art goniometer base, restrictions on reciprocal space coverage are also reduced. Conventional goniometer bases have only a fixed number of axes upon which the x-ray source, sample and detector move only in fixed planes. Incorporating robots to hold the detectors, x-ray source and/or sample allows for unrestricted motion anywhere in the robot's accessible envelope of reach. This also eliminates the need for specialty sample holders and attachments to provide additional range of motion for the sample.

By way of further background and explanation, over the years, a specialized field of materials analysis has developed in which x-rays are diffracted off of sample materials. Every crystalline material has a unique composition formed of regular, periodic spacings of electron densities. These are often referred to as "d-spacings" or "lattice spacings". Each compound has its own set of lattice spacings. Knowledge of these spacings is utilized to determine the compounds of which a particular material is composed. Additionally, it has been determined that stress in a material causes lattice spacings to expand or contract, as a result of compressive and tensile stress. If the composition of the material is known, the strain in a material can be measured by measuring the lattice spacing changes from the unstressed state. Further, if the grains in a material have a preferred orientation, rather than random orientation, variations in the intensity of the diffracted x-ray beam in certain directions will correspond to the grain orientation for that set of d-spacings. As a result, the orientation, sometimes called texture, of a material can be measured. The field of x-ray diffraction also enables measurement of other material properties such as crystallite size.

Operationally, when incident beam x-rays are diffracted from a material, they are diffracted in three dimensions, not in a plane. That is, when an incident x-ray beam hits a material, the diffracted x-rays actually form three-dimensional diffraction cones. Since each material is composed of many sets of d-spacings corresponding to the specific material being investigated, numerous diffraction cones are formed for any given material. Additionally, these diffraction cones have different diameters.

If the sample material is perfectly random, i.e., it has no preferred orientation, it is possible to obtain necessary information from any area on the diffraction cone. For randomly oriented materials, therefore, it is not necessary to move the detector and sample out of a given plane in order to observe and obtain the necessary information from various locations within the diffraction cone. To date, x-ray diffraction has primarily been performed on randomly oriented powdered materials in order to determine composition or on perfect, single crystals, in order to obtain a structure solution. As in most specialized fields, however, traditional applications are being extended to new methods and measurements. In the specialized field of x-ray diffraction, this is also true. Most sample materials of practical interest today do have some degree of preferred orientation. For example, semiconductor wafers, sputtering targets used to create those wafers, metals used to make aircraft or turbine blades, etc., all have some degree of preferred orientation. As x-ray diffraction has advanced to measure a material's properties, such as orientation and stress, it has become increasingly important and necessary to be able to access the entire diffraction cone.

Prior art response to this need has been the creation of two-dimensional (area) detectors, rather than a point or linear detector, so as to enable simultaneous coverage of a larger section of the diffraction cone. Further, it is known in the art to provide special sample holder attachments, often called circles or cradles, capable of moving the sample in an additional plane(s). By means of adding additional circles/cradles, in other words, it is possible to accomplish moving the sample to an increased range of positions by combining motions on numerous, independent axes moving in a circular plane. The primary system for these prior art x-ray diffraction analysis tools is a goniometer. On conventional goniometers, each independent movement is usually called an "axis". Most goniometers capable of collecting data on oriented sample materials have at least four independent axes (each moving in a plane and in a complete or partial circle) capable of positioning the sample in a given location relative to the incident x-ray beam. Further, the sample, detector and x-ray source are attached to and moved by the goniometer.

This solution to the problem is cumbersome, overly complex, and impractical to scale up, and critically, it restricts the sample size, weight and shape, since the sample must be held and moved by the goniometer base in the center of the goniometer circles (axes), all of which have fixed diameters. In this sense, the x-ray source, detector and sample are coupled. Because one of these circles, in the prior art, is holding and moving the detector and also holding, and possibly moving, the x-ray source, it is impossible to automatically vary either the x-ray source to sample distance or the sample to detector distance. In other words, in prior art devices, these distances are usually fixed on a given instrument. In one case known to the inventors, the sample to the detector distance is variable, but only manually and within a particular plane. In the SIEMENS brand area detector system devices, the detector is able to manually slide in or out on a fixed length arm attached to the horizontal plane circular axis. The detector still moves in a plane about the sample however, and can only be positioned at given distances (e.g., 6 cm, 15 cm, 20cm, or 30 cm) from the sample. Also, each time the detector is manually moved on the arm, new configuration parameters must be loaded, and the detector must be recalibrated.

Thus, there is a need in the art for providing an unrestricted motion apparatus and method for x-ray diffraction analysis enabling unrestricted coverage of the complete diffraction cone, which is capable of handling large, irregularly shaped samples, which eliminates the need for a variety of specialty sample holder "circles", and which allows the researcher to set up his or her own experiment without restriction. It, therefore, is an object of this invention to provide an unrestricted motion apparatus and method which provides for out-of-plane motion of the detector and/or x-ray source and simply and efficiently enables unrestricted coverage of the entire diffraction cone. A further object of the invention is to enable handling of large, at least over 12 cm in diameter, samples which may or may not be flat, and to enable the user to program his/her own unique data collection schemes.

SHORT STATEMENT OF THE INVENTION

Accordingly, the unrestricted motion apparatus for x-ray diffraction analysis of the present invention includes an x-ray source holding device capable of independent multi-dimensional movement for holding an x-ray source. A detector holding device capable of independent, multi-dimensional movement is provided for holding an x-ray detector. A sample holding device capable of independent, multi-dimensional movement is also, optionally, provided. A control means (e.g. computer) coordinates the motion of the sample holding device, the detector holding device, and the x-ray source holder so as to enable control of independent movements and operation of each. In other preferred embodiments, as desired, one of the three elements, i.e., sample holding device, detector holder, or x-ray source, is held stationary while the other two are enabled of independent, multi-dimensional motion. In a preferred embodiment, this multi-dimensional, independent motion is provided by means of robots. These robots, preferably, are programmable so that precise movement is enabled and locally empowered so that a user is not limited to vendor supplied software parameters or hardware restrictions. Additionally, the power and versatility of robots is utilized to enable testing of samples unlimited by size, weight and shape. While prior art devices are limited to analysis, essentially, of small regularly shaped samples, Applicants' invention is easily capable of handling large, as in over 12 cm in diameter, samples which may or may not be flat. In this way, the invention replaces the conventional goniometer base.

A corresponding method is also provided as disclosed and claimed more fully hereafter.

BRIEF DESCRIPTION OF THE DRAWINGS

Other objects, features, and advantages of the present invention will become more fully apparent from the following detailed description of the preferred embodiment, the appended claims, and the accompanying drawings in which:

DETAILED DESCRIPTION OF THE PREFERRED EMBODIMENT

Figure 1:
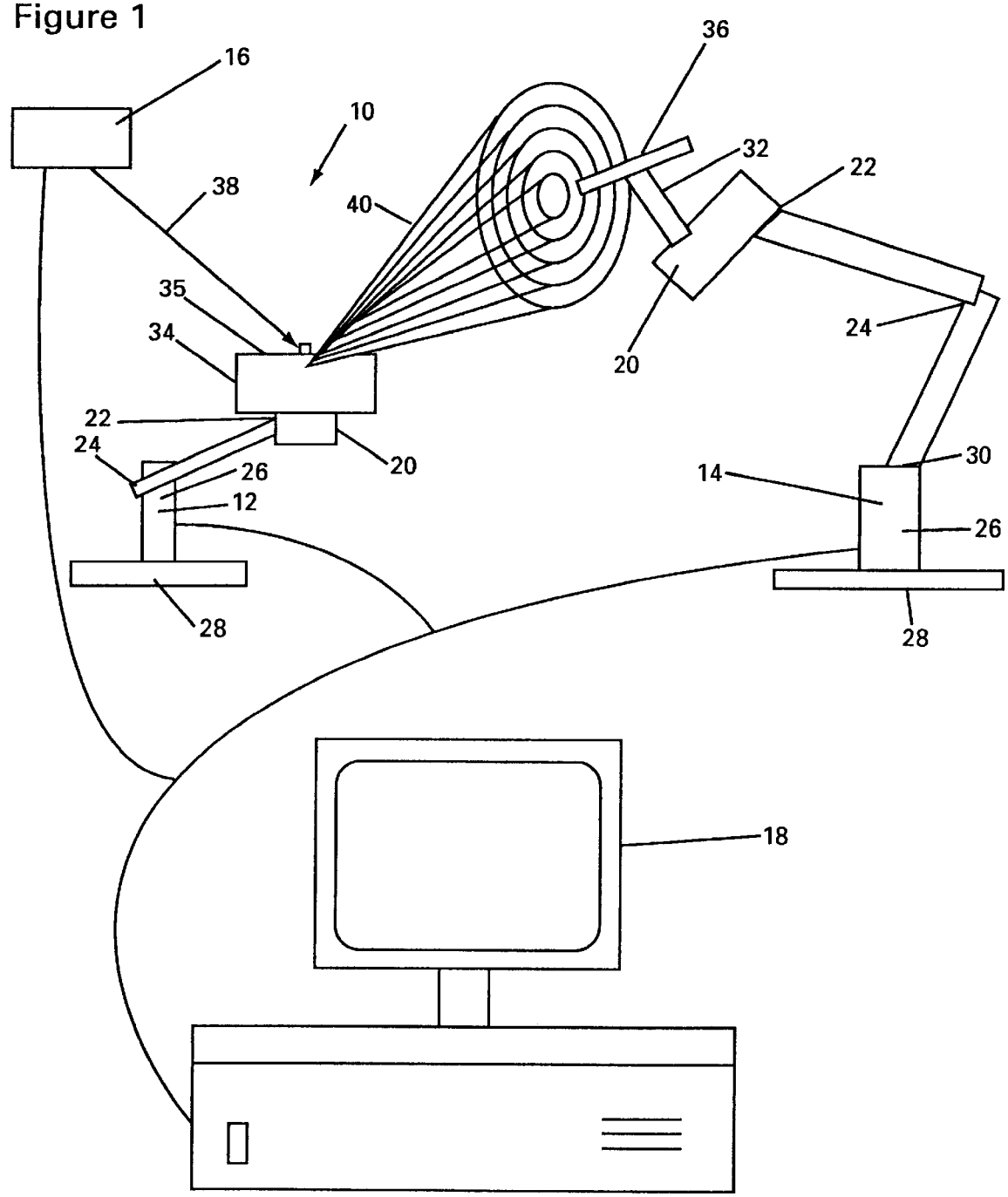
FIG. 1 is a front view of a preferred embodiment of the unrestricted motion apparatus of the present invention, in use obtaining measurements from multiple diffraction cones simultaneously.
Figure 2:
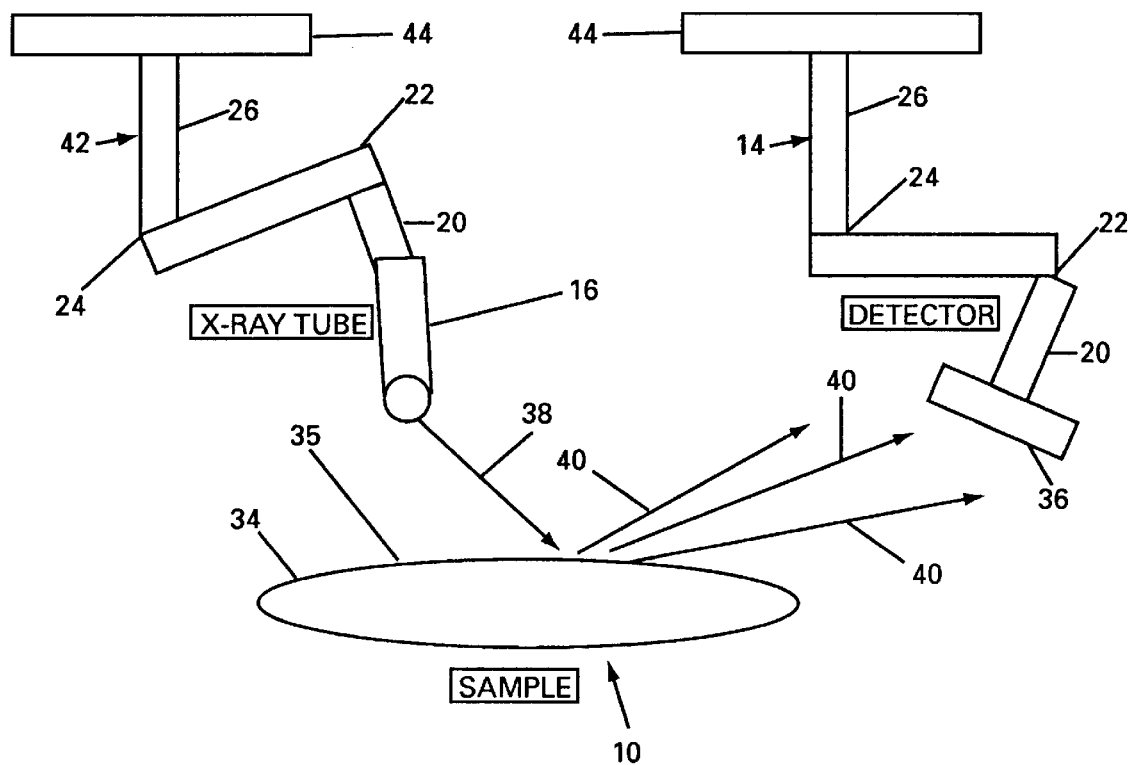
FIG. 2 is a front view of another preferred embodiment of the present invention wherein the sample is located on a rotational base and an x-y slide table and the x-ray source and detector are moved by robots.

The preferred embodiment of the present invention is illustrated by way of example in FIGS. 1–2. With specific reference to FIG. 1, an unrestricted motion apparatus 10 includes sample holder 12 and detector holder 14. Also, included is x-ray source 16 and controller 18.

Sample holder 12 and detector holder 14, in a preferred embodiment are robots. The robots are of any known design and include all or a subset of hand 20, wrist 22, elbow 24, support 26 and base 28. The industrial robot of the preferred embodiment can have as many flexible joints as just described as necessary to enable the required multi-dimensional movement. For example, detector holder 14 has, as may be desired, an additional joint 30 and extension 32.

Sample holder 12 is capable of accommodating any sample size, weight and shape. Sample 34, as shown in FIG. 1, is shown in a rectangular shape. Nonetheless, any sample 34 of any size, weight, and shape, large and/or irregular, is easily accommodated by sample holder 12 of the present invention.

Detector holder 14, as shown in FIG. 1, is shown holding detector 36. Detector 36 may be of any known type, such as a linear detector, a point detector, or an area detector.

Radiation source 16, in the preferred embodiment an x-ray source, creates an incident x-ray beam 38 which contacts sample 34, which creates diffraction cones 40 for examination. Because detector holder 14 is capable of moving detector 36 in multiple dimensions, the entire diffraction cone 40 is capable of being examined simply and efficiently. Because robots come in a wide range of sizes and are capable of precise, programmable movement, the sample size, shape and weight of sample 34 is no longer a problem. In fact, very large metal samples of about 1 meter in diameter, are easily accommodated as are, in fact, large samples of over 12 cm in diameter which may or may not be flat. Further, very large and heavy samples may remain stationary while the detector and x-ray source are moved about the sample as illustrated in FIG. 2.

Controller 18 is any known computer processor capable of programming. By means of controller 18, the movement of sample holder 12, detector holder 14, and the operation of x-ray source 16 are all facilitated. Because controller 18 is programmable, local control of the data collection scheme for various samples 34 is enabled. This feature allows a researcher to set up any type of experiment within the robot's accessible envelope without limitations imposed by vendor-supplied software. Prior to Applicants' invention the diffraction instrument vendor-supplied software, that a user had no choice but to use, only performed a fixed and limited number of data collection schemes. Applicants' invention overcomes the very real problem of the restrictive nature of prior art devices which were limited to vendor-supplied software and were not susceptible to local control and modification.

Referring now to FIG. 2, another preferred embodiment is disclosed. In this embodiment, x-ray source 16 is supported by x-ray source holder 42. X-ray source holder 42 and detector holder 14 are both supported by overhead supports 44. Further, in this embodiment, sample 34 is a very large sample, such as a sputtering target of about three feet in diameter. X-ray source holder 42 is a robot capable of independent movement, as is the sample holder 12 and detector holder 14, as previously described. In FIG. 2, sample 34 remains stationary or is located on a rotational base or is moveable on an x-y slide table (not shown) as desired. FIG. 2 shows a number of diffraction cones 40 illustrated by way of arrows, and illustrates the advantage of the unrestricted motion apparatus 10 of the present invention which enables complete examination of all areas on the diffraction cones 40.

Figure 3:
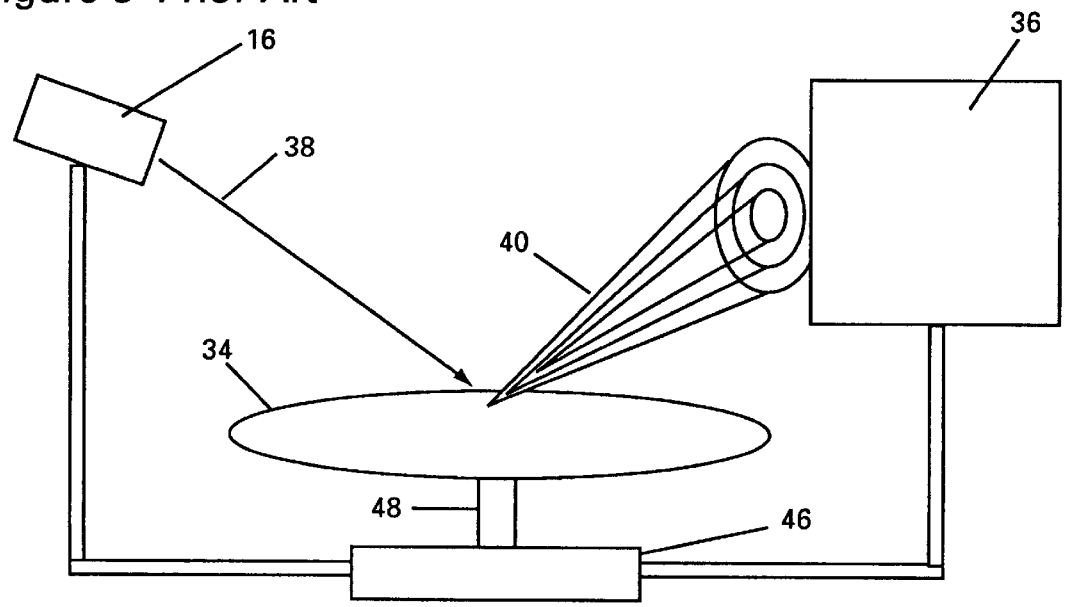
FIG. 3 is a front view illustration of a prior art goniometer.

By way of comparison, FIG. 3 illustrates prior art goniometers 46. As is known in the art, goniometers are extraordinarily expensive and complex devices designed to precisely hold and move a relatively small-sized sample 34, detector 36 and x-ray tube 16. FIG. 3 shows detector 36 which is rotatable in a horizontal plane only about point 48. Additionally, the sample 34 in prior devices, of any known type, is only capable of rotation in fixed planes such as a plane parallel to the goniometer base and a plane perpendicular to the goniometer base. Another failing of the prior art illustrated in FIG. 3 is that the x-ray source 16, sample 34, and detector 36 are all connected to and moved by the goniometer 46. As previously mentioned, in one case, detector 36 is capable of limited manual movement toward or away from sample 34, but is still held in a single fixed plane.

In operation, the unrestricted motion apparatus 10 of the present invention enables a user to select a sample 34, such as a sputtering target or a turbine blade, of any size, weight and shape, irregular or not, and place it on sample holder 12. In a preferred embodiment, the sample 34 is then exposed to an incident x-ray beam 38 so that incident x-ray beam 38 contacts sample 34 in a precise location, and resultantly creates diffraction cone 40 on the exposed surface side 35. As shown in FIG. 1, by means of independently moveable sample holder 12 and detector holder 14, detector 36 may be positioned on the exposed surface side 35 so as to examine the entire diffraction cone 40. While controller 18 has been disclosed in the preferred embodiment, it is obvious that the robots controlling sample holder 12 and detector holder 14, for example, could be individually moveable themselves. Also, the x-ray source 16 could be independently operable. In any event, for convenience, efficiency and accuracy, controller 18 is utilized to coordinate the movement and operation of all the parts of this invention so that individualized, unique data collection schemes are possible.

In another preferred embodiment, sample 34 is placed on a stationary support or on a support that rotates and/or moves only in the x-y direction as may be desired. In any event, in this embodiment, the x-ray source 16 and detector 36, instead of sample 34, are held by robots capable of independent, multi-dimensional movement. In fact, any combination wherein two of the major elements, x-ray source, sample holder or detector, are decoupled is appropriate. That is, it is also envisioned that x-ray source 16 and sample 34 are attached to robots and detector 36 is held stationery. The result is the same in that the user has unrestricted coverage of the complete diffraction cone 40, large samples, over 12 cm in diameter and of irregular shape are easily handled, and controller 18 enables customization of data collection schemes as desired or necessary. Additionally, a preferred embodiment of the invention includes the ability to automatically change samples 34. In prior art, robots have been used to change samples for a variety of analytical applications. The primary embodiment of this invention is not to merely change samples, but automatic sample changing is an additional advantage. Since robots are programmable and have customizable "hands" or sample grippers, the robots are easily used to put down the completed sample and pick up a new or next sample between measurements.

A method for measuring the entire diffraction cone 40 of sample 34 includes the steps of providing an independently, robotically-controlled x-ray source holder 42 and x-ray source 16 and independent, robotically-controlled sample holder 12, in conjunction with an independently, robotically-controlled detector holder 14. Both holders 12 and 14 are capable of independent, multi-dimensional movement. A sample 34 is placed on sample holder 12, in the method, and is irradiated by the x-ray source 16 so that a diffraction cone 40 is created on the exposed surface side 35. Robotically-controlled detector 36 is then maneuvered within the diffraction cone 40 for analysis of the diffraction cone 40 on the exposed surface side 35.

Many additional applications and advantages are provided by the invention. In particular, it is, by way of the unrestricted motion apparatus 10, possible to automatically map multiple specific areas on large samples without manually repositioning the sample. It is also possible to isolate and analyze any specific area on a large sample. In this sense, unrestricted motion apparatus 10 enables x, y, and z motion, as well as three dimensional motion about any x, y, z point. In the trade, this is called microdiffraction analysis. Further, by way of the unrestricted motion apparatus 10, x-ray source 16 can be automatically changed from a point source to a line source by simply rotating the robot hand held x-ray source 16 by 90°. A process that was time consuming and cumbersome in the prior art is reduced to an automatically enabled feature of the present invention.

While the present invention has been disclosed in connection with the preferred embodiments thereof, it should be understood that there may be other embodiments which fall within the spirit and scope of the invention as defined by the following claims.

We claim:

1. In the field of materials analysis where radiation diffraction is used to create three dimensional diffraction cones for analysis of properties of a sample of material, an unrestricted motion diffraction apparatus comprising:
    (a) an independent sample holding means for holding a sample, said sample having an exposed surface side;
    (b) a radiation source for creating a reflected diffraction cone from the sample on the exposed surface side;
    (c) an independent radiation source holding means for holding said radiation source on the exposed surface side of said sample;
    (d) a radiation detector for analyzing said reflected diffraction cone;
    (e) an independent radiation detector holding means for holding said radiation detector on the same side of said sample as said radiation source; and
    (f) control means connected to said radiation source and said radiation source holding means and said radiation detector and said radiation detector holding means and said sample holding means for separately controlling the independent, unrestricted, multidimensional movement and operation of at least one of said sample holding means, said radiation source holding means, and said radiation detector holding means and controlling the operation of said radiation source and said radiation detector.

2. In the field of materials analysis where radiation diffraction is used to create three dimensional diffraction cones for analysis of properties of a sample of material, an unrestricted motion diffraction apparatus comprising:
    (a) an independent sample holding means for holding a sample, said sample having an exposed surface side;
    (b) a radiation source for creating a reflected diffraction cone from the sample on the exposed surface side;
    (c) an independent radiation source holding means for holding said radiation source on the exposed surface side of said sample and for providing independent, unrestricted, multi-dimensional movement of said radiation source;
    (d) a radiation detector for analyzing said reflected diffraction cone;
    (e) an independent radiation detector holding means for holding said radiation detector on the same side of said sample as said radiation source and for providing independent, unrestricted, multi-dimensional movement of said radiation detector throughout said diffraction cone; and (f) control means connected to said radiation source and said radiation source holding means and said radiation detector and said radiation detector holding means for separately controlling the independent, unrestricted, multi-dimensional movement and operation of said radiation source holding means and said radiation detector holding means and said radiation source and said radiation detector.

3. The apparatus of claim 2 wherein said independent sample holding means further comprises an independent sample holding means for providing independent, unrestricted, multi-dimensional movement of said sample connected to said control means.

4. The apparatus of claim 2 wherein said radiation source further comprises an x-ray source.

5. A method for unrestricted analysis of the entire diffraction cone of sample materials comprising the steps of:

(a) selecting a sample of material to be analyzed, said sample having an exposed surface side;

(b) providing an independent, robotically-controlled, unrestricted motion radiation source on the exposed surface side of said sample;

(c) providing an independent, robotically-controlled, unrestricted motion sample holder;

(d) placing the sample on said sample holder;

(e) radiating the exposed surface of said sample with radiation by said radiation source so as to create a diffraction cone on the exposed surface side of said sample;

(f) providing an independent, robotically-controlled, unrestricted motion detector for analyzing said diffraction cone; and (g) moving said robotically-controlled, unrestricted motion detector so as to obtain unrestricted coverage of the complete diffraction cone on the exposed surface side of said sample.

6. The method of claim 5 further comprising the step of connecting a programmable controller means for providing local, reprogrammable, independent control of said independent, robotically-controlled, unrestricted motion sample holder, detector holder, radiation source holder and said radiation source and detector.

7. The method of claim 5 wherein the step of providing a radiation source comprises the step of providing an x-ray source.

* * * * *